United States Patent
Thiriveedhi et al.

(10) Patent No.: US 11,414,421 B2
(45) Date of Patent: Aug. 16, 2022

(54) PROCESS FOR THE PREPARATION OF RIBOCICLIB SUCCINATE AND ITS NOVEL CRYSTALLINE FORMS THEREOF

(71) Applicant: NATCO PHARMA LTD, Hyderabad (IN)

(72) Inventors: Arunkumar Thiriveedhi, Hyderabad (IN); Swapna Kondaveeti, Hyderabad (IN); Sathish Thumati, Hyderabad (IN); Naresh Ghanta, Hyderabad (IN); Janaki Rama Rao Ravi, Hyderabad (IN); Durga Prasad Konakanchi, Hyderabad (IN); Pulla Reddy Muddansani, Hyderabad (IN); Venkaiah Chowdary Nannapaneni, Hyderabad (IN)

(73) Assignee: NATCO PHARMA LTD, Hyderabad (IN)

( * ) Notice: Subject to any disclaimer, the term of this patent is extended or adjusted under 35 U.S.C. 154(b) by 0 days.

(21) Appl. No.: 16/962,934

(22) PCT Filed: Jan. 10, 2019

(86) PCT No.: PCT/IN2019/050019
§ 371 (c)(1),
(2) Date: Jul. 17, 2020

(87) PCT Pub. No.: WO2019/142206
PCT Pub. Date: Jul. 25, 2019

(65) Prior Publication Data
US 2021/0122754 A1    Apr. 29, 2021

(30) Foreign Application Priority Data

Jan. 20, 2018 (IN) .............................. 201841002392

(51) Int. Cl.
*C07D 487/04* (2006.01)
(52) U.S. Cl.
CPC ........ *C07D 487/04* (2013.01); *C07B 2200/13* (2013.01)
(58) Field of Classification Search
CPC .................................................. C07D 487/04
USPC ........................................................ 544/280
See application file for complete search history.

(56) References Cited

U.S. PATENT DOCUMENTS 9,193,732 B2   11/2015   Calienni et al.

FOREIGN PATENT DOCUMENTS

| CN | 106478641 A | 3/2017 |
| IN | 201741000072 A | 7/2018 |
| WO | 2012/064805 A1 | 5/2012 |
| WO | 2019/019959 A1 | 1/2019 |

OTHER PUBLICATIONS

International Search Report and Written Opinion dated Apr. 11, 2019 from International Application No. PCT/IN2019/050019 (Authorized officer, Parameswar Sau), 9 pages.

*Primary Examiner* — Douglas M Willis
(74) *Attorney, Agent, or Firm* — MH2 Technology Law Group, LLP

(57) ABSTRACT

The present invention relates to an improved process for the preparation of 7-cyclopentyl-N,N-dimethyl-2-{[5-(piperazin-1-yl)pyridin-2-yl]amino}-7H-pyrrolo[2,3-d]pyrimidine-6-carboxamide succinate (1/1) compound of formula-1a and its novel crystalline forms. The said compound of formula-1a is represented by the following structural formula: Formula-1a

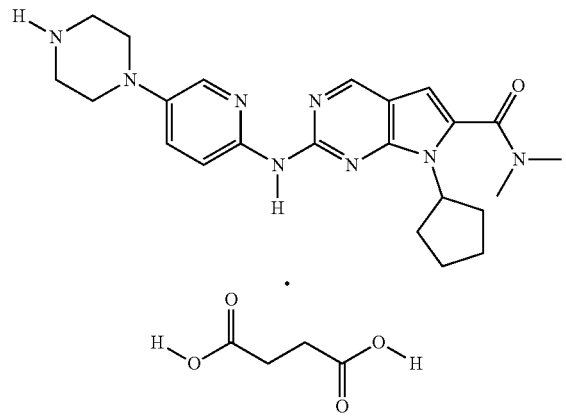

Formula-1a 8 Claims, 4 Drawing Sheets

PROCESS FOR THE PREPARATION OF RIBOCICLIB SUCCINATE AND ITS NOVEL CRYSTALLINE FORMS THEREOF

CROSS-REFERENCE TO RELATED APPLICATIONS

This application is a U.S. National Stage application of PCT/IN2019/050019 filed 10 Jan. 2019, which claims priority to Indian Application No. 201841002392 filed 20 Jan. 2018, the entire disclosures of which are hereby incorporated by reference in their entireties.

FIELD OF THE INVENTION

The present invention relates to an improved process for the preparation of 7-cyclopentyl-N,N-dimethyl-2-{[5-(piperazin-1-yl)pyridin-2-yl]amino}-7H-pyrrolo [2,3-d]pyrimidine-6-carboxamide succinate (1/1) compound of formula-1a and its novel crystalline forms. The said compound of formula-1a is represented by the following structural formula:

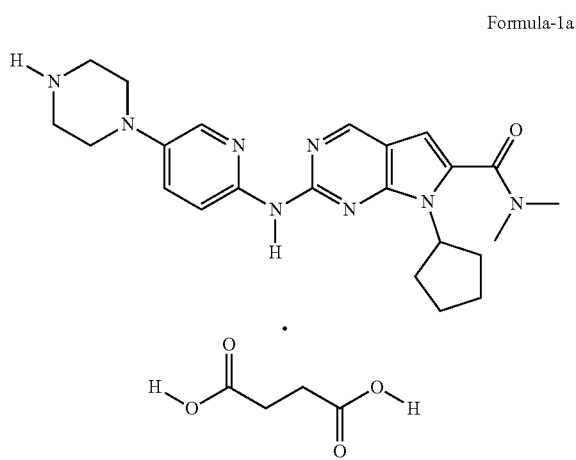 [SMILES: CN(C)C(=O)c1cc2cnc(Nc3ccc(N4CCNCC4)cn3)nc2n1C1CCCC1 ; O=C(O)CCC(=O)O]

Formula-1a

The present invention also involves the usage low cost reagents, solvents and the process conditions which can be easily adopted for commercial scale.

BACKGROUND OF THE INVENTION

The 7-cyclopentyl-N,N-dimethyl-2-{[5-(piperazin-1-yl)pyridin-2-yl]amino}-7H-pyrrolo [2,3-d]pyrimidine-6-carboxamide succinate (1/1) is commonly known as Ribociclib succinate. Ribociclib succinate was developed by Novartis and Astex Pharmaceuticals which is an anticancer agent useful for the treatment of certain kinds of breast cancers. The trade name of Ribociclib succinate is Kisqali, dosage form is tablet.

U.S. Pat. No. 9,193,732 (Applicant: Novartis AG and Astex Pharmaceuticals) disclosed two physical forms namely hydrate and non-hydrate forms of Ribociclib succinate of formula-1a. Ribociclib succinate was prepared by treating Ribociclib base of formula-1 with succinic acid in isopropyl alcohol. The resulting Ribociclib succinate was subjected to relative humidity 0-90-0% RH and 0-80-0% RH. Ribociclib succinate absorbs moisture up to 2.0% at 0-90-0% RH and up to 0.5% at 0-90-0% RH. Dynamic Vapour sorption (DVS), PXRD, DSC and Thermogravimetric analysis of these two hydrate and non-hydrate forms of Ribociclib succinate of formula-1a were also discussed. However, when following the proposed route of synthesis the obtained Ribociclib has low yield and purity. Hence, there is a need in the art to develop an alternate and improved process for the preparation Ribociclib succinate which enhances the yield and purity of the desired compound.

Polymorphism, the occurrence of different crystal forms, is a property of some molecules and molecular complexes. A single molecule, may give rise to a variety of crystalline forms having distinct crystal structures and physical properties like melting point, X-ray diffraction pattern, infrared absorption fingerprint, and solid state NMR spectrum, thermogravimetric analysis ('TGA'), and differential scanning calorimetry ('DSC') which have been used to distinguish polymorphic forms.

The difference in the physical properties of different crystalline forms result from the orientation and intermolecular interactions of adjacent molecules or complexes in the bulk solid. Accordingly, polymorphs are distinct solids sharing the same molecular formula yet having distinct advantageous physical properties compared to other crystalline forms of the same compound or complex.

One of the most important physical properties of pharmaceutical compounds is their solubility in aqueous solution, particularly their solubility in the gastric juices of a patient. For example, where absorption through the gastrointestinal tract is slow, it is often desirable for a drug that is unstable to conditions in the patient's stomach or intestine to dissolve slowly so that it does not accumulate in a deleterious environment. Different crystalline forms or polymorphs of the same pharmaceutical compound can reportedly do have different aqueous solubility. Pharmaceutical compounds having different crystalline forms or polymorphs have different dissolution property. It enlarges the repertoire of materials that a formulation scientist has available for designing, for example, a pharmaceutical dosage form of a drug with a targeted release profile or other desired characteristic features.

The discovery of new crystalline or polymorphic forms of a pharmaceutically useful compound provides a new opportunity to improve the performance characteristics of a pharmaceutical product.

Hence, there is a significant need in the art to develop novel polymorphs of Ribociclib succinate which are stable and also improves the performance characteristics of a pharmaceutical product.

The present inventors have developed novel crystalline forms of Ribociclib succinate and its process for preparation thereof.

BRIEF SUMMARY OF THE INVENTION

The first aspect of the present invention is to provide an improved process for the preparation of Ribociclib succinate compound of formula-1a.

The second aspect of the present invention is to provide a novel crystalline form of Ribociclib succinate compound of formula-1a hereinafter designated as "Form-A" and its process for the preparation thereof.

The third aspect of the present invention is to provide a novel crystalline form of Ribociclib succinate compound of formula-1a hereinafter designated as "Form-B" and its process for the preparation thereof.

The fourth aspect of the present invention is to provide a novel crystalline form of Ribociclib succinate compound of formula-1a hereinafter designated as "Form-C" and its process for the preparation thereof.

The fifth aspect of the present invention is to provide a novel crystalline form of Ribociclib succinate compound of formula-1a hereinafter designated as "Form-D" and its process for the preparation thereof.

The sixth aspect of the present invention is to provide a novel crystalline form of Ribociclib succinate compound of formula-1a hereinafter designated as "Form-E" and its process for the preparation thereof.

The seventh aspect of the present invention is to provide a novel crystalline form of Ribociclib succinate compound of formula-1a hereinafter designated as "Form-N" and its process for the preparation thereof.

BRIEF DESCRIPTION OF THE DRAWINGS

FIG. 1: Illustrates a characteristic PXRD pattern of crystalline Form-A of Ribociclib succinate compound of formula-1a.

FIG. 2: Illustrates a characteristic PXRD pattern of crystalline Form-B of Ribociclib succinate compound of formula-1a.

FIG. 3: Illustrates a characteristic PXRD pattern of crystalline Form-C of Ribociclib succinate compound of formula-1a.

FIG. 4: Illustrates a characteristic PXRD pattern of crystalline Form-D of Ribociclib succinate compound of formula-1a.

FIG. 5: Illustrates a characteristic PXRD pattern of crystalline Form-E of Ribociclib succinate compound of formula-1a.

FIG. 6: Illustrates a characteristic PXRD pattern of crystalline Form-N of Ribociclib succinate compound of formula-1a.

FIG. 7: Illustrates DSC thermogram of crystalline Form-N of Ribociclib succinate compound of formula-1a.

ADVANTAGES OF THE INVENTION

Figure 1:
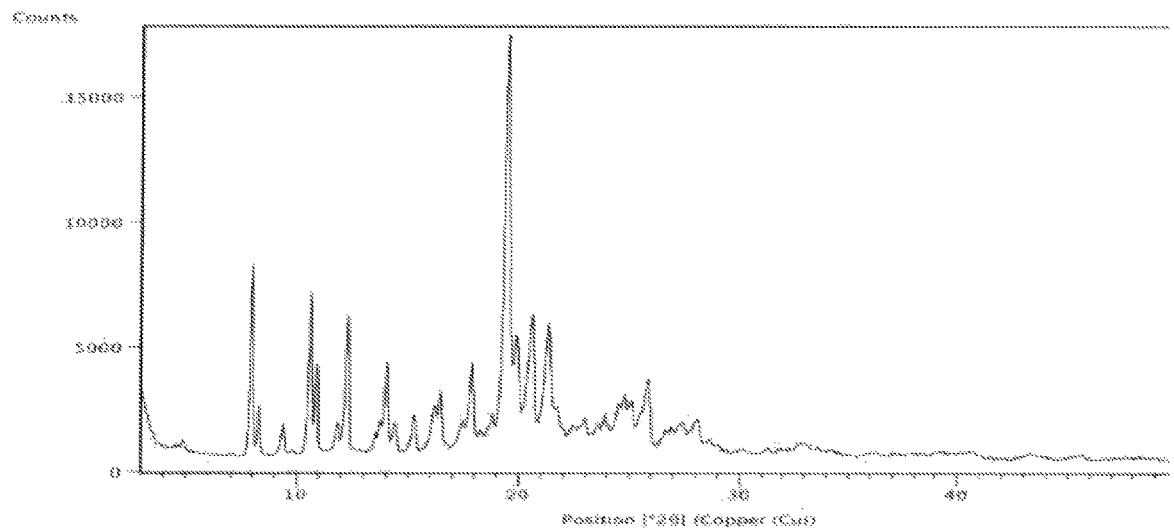

The present invention avoids the usage of expensive agents like HBTU, Tris(dibenzylideneacetone) dipalladium(O) (Pd$_2$(dba)3), (+/−)-2,2'-Bis(diphenyl phosphino)-1,1'-binaphthyl(BINAP).

The present invention involves the usage of low cost reagents and solvents which decreases the cost of production and suitable for the commercial scale process.

The process of the present invention provides Ribociclib succinate with high yield and purity.

DETAILED DESCRIPTION OF THE INVENTION

The term "suitable solvent" used in the present invention refers to "hydrocarbon solvents" selected from aliphatic hydrocarbon solvents such as n-hexane, n-heptane, cyclohexane, petroleum ether and aromatic hydrocarbon solvents such as benzene, toluene, xylene and the like; "ether solvents" such as dimethyl ether, diisopropyl ether, diethyl ether, methyl tert-butyl ether, 1,2-dimethoxy ethane, tetrahydrofuran, 1,4-dioxane, monoglyme, diglyme and the like; "ester solvents" such as methyl acetate, ethyl acetate, isopropyl acetate, n-butyl acetate and the like; "polar-aprotic solvents such as dimethylacetamide, dimethylformamide, dimethylsulfoxide, N-methylpyrrolidone (NMP) and the like; "chloro solvents" such as dichloromethane, dichloroethane, chloroform, carbon tetrachloride and the like; "ketone solvents" such as acetone, methyl ethyl ketone, methyl isobutyl ketone and the like; "nitrile solvents" such as acetonitrile, propionitrile, isobutyronitrile and the like; "alcoholic solvents" such as methanol, ethanol, n-propanol, isopropanol, n-butanol, isobutanol, t-butanol and the like; "polar solvents" such as water or mixtures thereof.

As used herein the present invention, the term "antisolvent" refers to a solvent which is used to precipitate the solid from a solution.

As used herein the present invention the term "suitable base" refers to "alkali metal carbonates" such as sodium carbonate, potassium carbonate, lithium carbonate and the like; "alkali metal bicarbonates" such as sodium bicarbonate, potassium bicarbonate and the like; "alkali metal hydroxides" such as sodium hydroxide, potassium hydroxide, lithium hydroxide and the like; "alkali metal alkoxides" such as sodium methoxide, sodium ethoxide, potassium methoxide, potassium ethoxide, sodium tert.butoxide, potassium tert.butoxide, lithium tert.butoxide and the like; alkali metal hydrides such as sodium hydride, potassium hydride, lithium hydride and the like; alkali metal amides such as sodium amide, potassium amide, lithium amide and the like; and organic bases like dimethylamine, diethylamine, diisopropylamine, diisopropylethylamine, diisobutylamine, triethylamine, pyridine, 4-dimethylaminopyridine (DMAP), N-methyl morpholine (NMM), 2,6-lutidine, lithium diisopropylamide; organosilicon bases such as lithium hexamethyldisilazide (LiHMDS), sodium hexamethyldisilazide (NaHMDS), potassium hexamethyldisilazide (KHMDS) or mixtures thereof.

The first aspect of the present invention is to provide an improved process for the preparation of Ribociclib succinate compound of formula-1a, comprising of:
  a) Reacting 2-Chloro-7-cyclopentyl-7H-pyrrolo[2,3-d] pyrimidine-6-carboxylic acid compound of formula-2 with dimethylamine in presence of a suitable coupling agent, suitable base in a suitable solvent to provide 2-chloro-7-cyclopentyl-N,N-dimethyl-pyrrolo[2,3-d] pyrimidine-6-carboxamide compound of formula-3,
  b) reacting the compound of formula-3 with 4-(6-aminopyridine-3-yl)-piperazine-1-carboxylic acid tert-butyl ester compound of formula-4 in presence of a suitable base in a suitable solvent to provide tert-butyl 4-[6-[[7-cyclopentyl-6-(dimethylcarbamoyl) pyrrolo[2,3-d]pyrimidin-2-yl]amino]-3-pyridyl]piperazine-1-carboxylate compound of formula-5,
  c) treating the compound of formula-5 with a suitable acid, optionally in a suitable solvent to provide Ribociclib compound of formula-1,
  d) optionally, purifying the compound obtained in step-c) with a suitable solvent,
  e) treating the Ribociclib compound of formula-1 obtained from step-c) or step-d) with succinic acid in a suitable solvent or mixture of solvents provides Ribociclib succinate compound of formula-1a.

Wherein, in step-a), the suitable coupling reagent is selected from hydroxybenzotriazole (HOBt), 1-ethyl-3-(3-dimethylaminopropyl)carbodiimide hydrochloride (EDCHCl), benzotriazol-1-yl-oxytripyrrolidinophosphonium hexafluorophosphate (PyBOP), Bromo-trispyrrolidino phosphonium hexafluorophosphate (PyBrOP), O-(benzotriazol-1-yl)-N,N,N',N'-tetramethyluronium tetrafluoroborate (TBTU), 2-(1H-Benzotriazol-1-yl)-1,1,3,3-tetramethyluronium hexafluorophosphate (HBTU), thionyl chloride, 1-[bis (dimethylamino)methylene]-1H 1,2,3-triazolo[4,5-b]pyridinium 3-oxide hexafluorophosphate (HATU), 1-cyano-2- ethoxy-2-oxoethylidenaminooxy) dimethylamino-morpholino-carbenium hexafluorophosphate (COMU) and tetramethylfluoroformamidinium hexafluorophosphate (TFFH) or mixtures thereof in the presence of a base selected from triethylamine, diisopropyl ethylamine (DIPEA), N-methylmorpholine (NMM), pyridine and the like.

In step-b), the suitable base is selected from organosilicon bases as defined above.

In step-c), the suitable acid is selected from inorganic acid such as hydrochloric acid or its aqueous solution.

In step a) to e), the suitable solvent is selected from ether solvents, chloro solvents, ester solvents, alcohol solvents, ketone solvents, polar aprotic solvents, hydrocarbon solvents, nitrile solvents and polar solvents such as water or mixtures thereof.

In the present invention, the expensive coupling reagent N,N,N',N'-Tetramethyl-O-(1H-benzotriazol-1-yl)uronium hexafluorophosphate (HBTU) is replaced with N-(3-Dimethylaminopropyl)-N'-ethylcarbodiimide hydrochloride (EDC HCl) and hydroxybenzotriazole (HOBt) to prepare compound of formula-3. Further, coupling of compound of formula-3 with 4-(6-amino-pyridin-3-yl)-piperazine-1-carboxylic acid tert-butyl ester of formula-4 is achieved with lithium hexamethyldisilazane (1M solution in tetrahydrofuran) to give tert-butyl4-[6-[[7-cyclopentyl-6-(dimethylcarbamoyl)pyrrolo[2,3-d]pyrimidin-2-yl]amino]-3-pyridyl]piperazine-1-carboxylate of formula-5 with >80% of yield by theory, purity by HPLC>98.0% and the present process also avoiding highly expensive and less stable reagents like Tris(dibenzylideneacetone) dipalladium(0) (Pd$_2$(dba)3), (+/−)-2,2'-Bis(diphenylphosphino)-1,1'-binaphthyl (BINAP) and sodium tert-butoxide.

In a preferred embodiment of the present invention provides an improved process for the preparation of Ribociclib succinate compound of formula-1a, comprising of:
  a) Reacting 2-Chloro-7-cyclopentyl-7H-pyrrolo[2,3-d]pyrimidine-6-carboxylic acid compound of formula-2 with dimethylamine in presence of N-(3-Dimethylaminopropyl)-N'-ethylcarbodiimide hydrochloride (EDC HCl), hydroxybenzotriazole (HOBt) and N-methylmorpholine in dimethylformamide provides 2-chloro-7-cyclopentyl-N,N-dimethyl-pyrrolo [2,3-d]pyrimidine-6-carboxamide compound of formula-3,
  b) reacting the compound of formula-3 with 4-(6-amino-pyridine-3-yl)-piperazine-1-carboxylic acid tert-butyl ester compound of formula-4 in presence of lithium hexamethyldisilazide (LiHMDS) in toluene provides tert-butyl 4-[6-[[7-cyclopentyl-6-(dimethylcarbamoyl)pyrrolo[2,3-d]pyrimidin-2-yl]amino]-3-pyridyl]piperazine-1-carboxylate compound of formula-5,
  c) treating the compound of formula-5 with aqueous hydrochloric acid provides Ribociclib compound of formula-1,
  d) purifying the compound obtained in step-c) with isopropyl alcohol or methanol,
  e) treating the Ribociclib compound of formula-1 obtained from step-c) or step-d) with succinic acid in aqueous tetrahydrofuran provides Ribociclib succinate compound of formula-1a.

In another preferred embodiment of the present invention provides an improved process for the preparation of Ribociclib succinate compound of formula-1a, comprising of:
  a) Treating 2-Chloro-7-cyclopentyl-7H-pyrrolo[2,3-d]pyrimidine-6-carboxylic acid compound of formula-2 with thionyl chloride followed by reacting the obtained compound with dimethylamine in presence of triethylamine in a mixture of toluene and tetrahydrofuran provides 2-chloro-7-cyclopentyl-N,N-dimethyl-pyrrolo[2,3-d]pyrimidine-6-carboxamide compound of formula-3,
  b) reacting the compound of formula-3 with 4-(6-amino-pyridin-3-yl)-piperazine-1-carboxylic acid tert-butyl ester compound of formula-4 in presence of lithium hexamethyldisilazide (LiHMDS) in toluene provides tert-butyl 4-[6-[[7-cyclopentyl-6-(dimethylcarbamoyl)pyrrolo[2,3-d]pyrimidin-2-yl]amino]-3-pyridyl]piperazine-1-carboxylate compound of formula-5,
  c) treating the compound of formula-5 with aqueous hydrochloric acid provides Ribociclib compound of formula-1,
  d) purifying the compound obtained in step-c) with methanol,
  e) treating the Ribociclib compound of formula-1 obtained from step-c) or step-d) with succinic acid in aqueous tetrahydrofuran provides Ribociclib succinate compound of formula-1a.

The second aspect of the present invention is to provide crystalline Form-A of Ribociclib succinate compound of formula-1a, which is characterized by:
  i) Its powder X-ray diffractogram having peaks at about 7.96, 8.30, 10.62, 10.93, 12.31, 14.09, 16.17, 16.45, 17.92, 19.53, 19.94, 20.64, 21.37, 24.49, 24.79, 25.12 and 25.89±0.2 degrees 2-theta.
  ii) powdered X-ray diffraction pattern as shown in FIG. 1.

Figure 2:
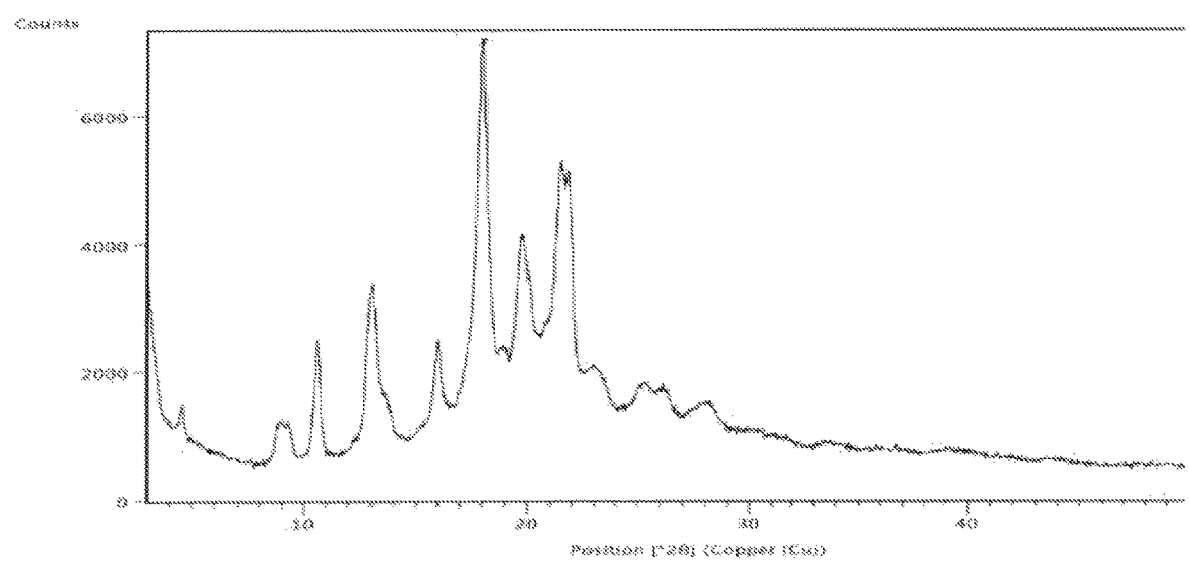

The third aspect of the present invention is to provide crystalline Form-B of Ribociclib succinate compound of formula-1a, which is characterized by:
  i) Its powder X-ray diffractogram having peaks at about 10.62, 12.93, 13.09, 15.98, 18.02, 19.03, 19.72, 21.43, 21.86, and 23.19±0.2 degrees 2-theta.
  ii) powdered X-ray diffraction pattern as shown in FIG. 2.

Figure 3:
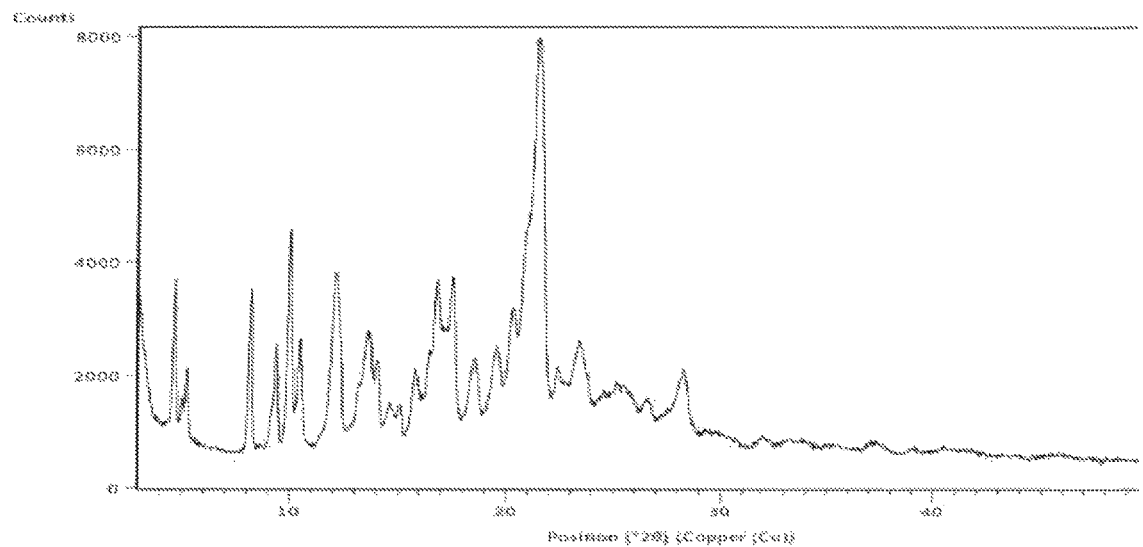

The fourth aspect of the present invention is to provide crystalline Form-C of Ribociclib succinate compound of formula-1a, which is characterized by:
  i) Its powder X-ray diffractogram having peaks at about 4.69, 5.00, 5.24, 8.18, 9.38, 10.03, 10.48, 12.10, 12.35, 13.17, 13.58, 13.74, 14.09, 15.78, 16.40, 16.83, 17.56, 18.62, 19.57, 20.37, 20.87, 21.68, 22.38, 23.46 and 28.26±0.2 degrees 2-theta.
  ii) powdered X-ray diffraction pattern as shown in FIG. 3.

Figure 4:
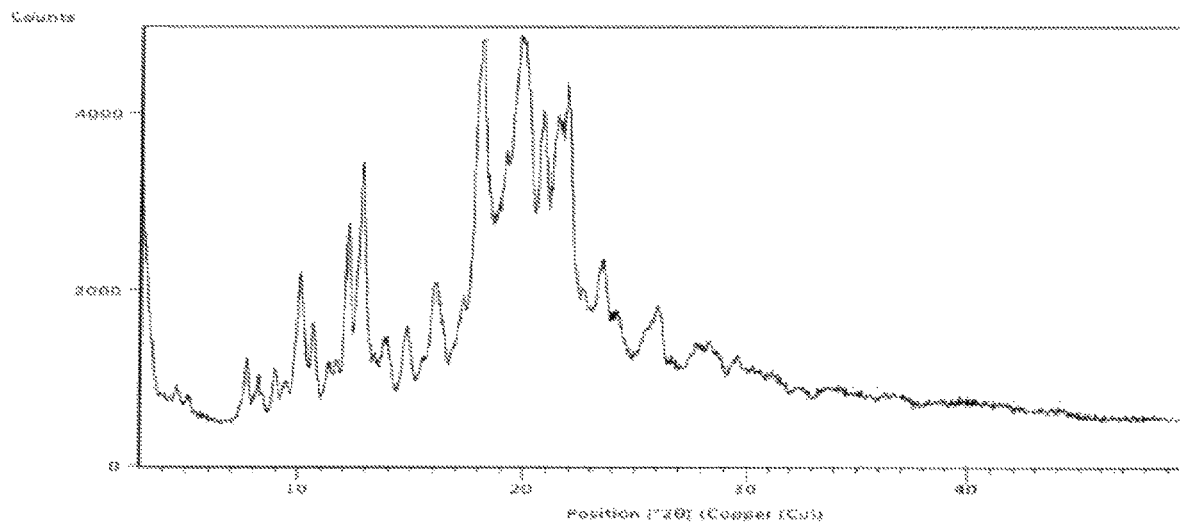

The fifth aspect of the present invention is to provide crystalline Form-D of Ribociclib succinate compound of formula-1a, which is characterized by:
  i) Its powder X-ray diffractogram having peaks at about 7.68, 8.19, 8.98, 10.08, 10.64, 11.33, 12.21, 12.90, 13.91, 14.78, 15.97, 17.30, 17.89, 18.21, 19.24, 19.84, 20.89, 21.48, 21.93, 23.57, 24.23, 26.13, and 28.41±0.2 degrees 2-theta.
  ii) powdered X-ray diffraction pattern as shown in FIG. 4.

Figure 5:
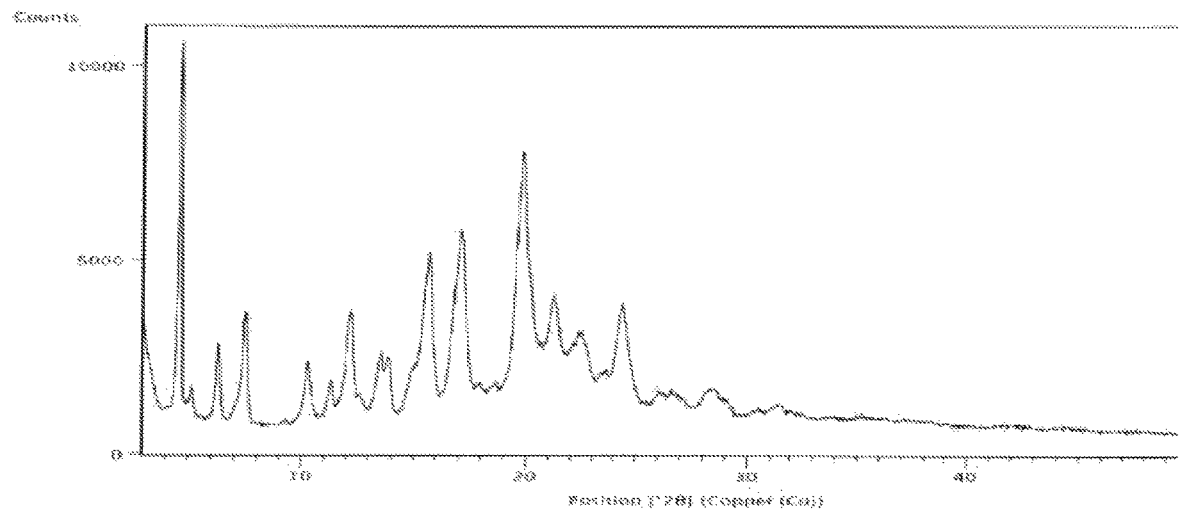

The sixth aspect of the present invention is to provide crystalline Form-E of Ribociclib succinate compound of formula-1a, which is characterized by:
  i) Its powder X-ray diffractogram having peaks at about 4.64, 6.31, 7.51, 10.26, 11.34, 12.23, 13.56, 13.94, 15.71, 17.14, 19.90, 21.23, 22.48 and 24.42±0.2 degrees 2-theta.
  ii) powdered X-ray diffraction pattern as shown in FIG. 5.

Further, the present invention also provides a process for the preparation of crystalline Form-A, B, C, D & E of Ribociclib succinate compound of formula-1a, comprising of:
  a) Suspending Ribociclib compound of formula-1 in a suitable solvent, b) heating the reaction mixture to a suitable temperature,
c) adding a solution of succinic acid in a solvent to the reaction mixture,
d) stirring the reaction mixture,
e) cooling the reaction mixture to a suitable temperature,
f) filtering the obtained solid to get corresponding crystalline form of Ribociclib succinate compound of formula-1a.

Wherein in step-a) & c), the suitable solvent is selected from ether solvents, chloro solvents, ester solvents, alcohol solvents, ketone solvents, polar aprotic solvents, hydrocarbon solvents, nitrile solvents and polar solvents such as water or mixtures thereof.

Figure 6:
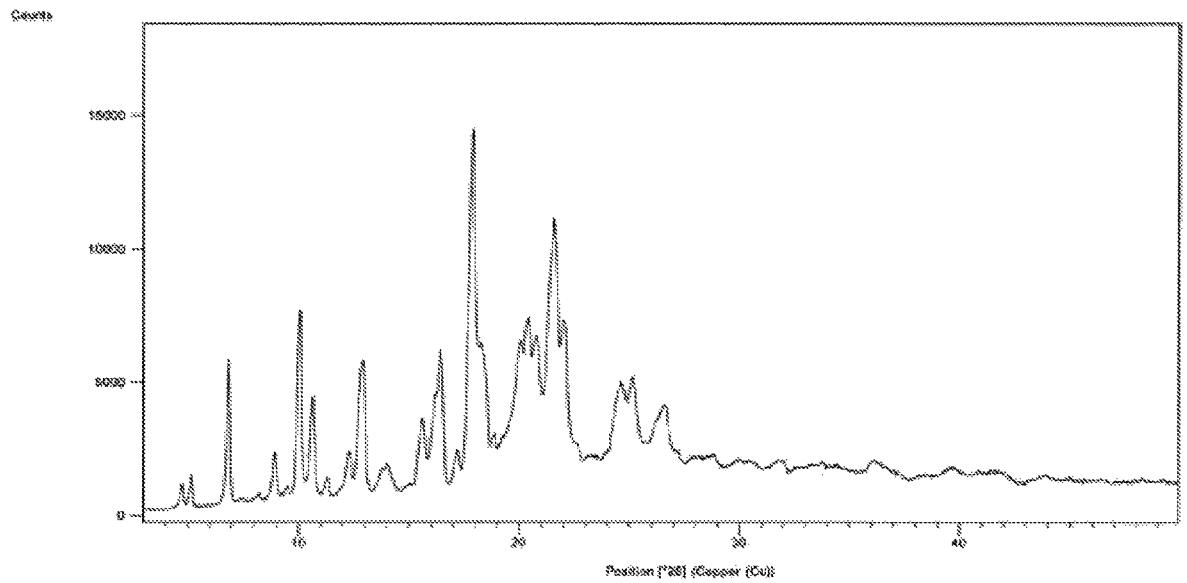
Figure 7:
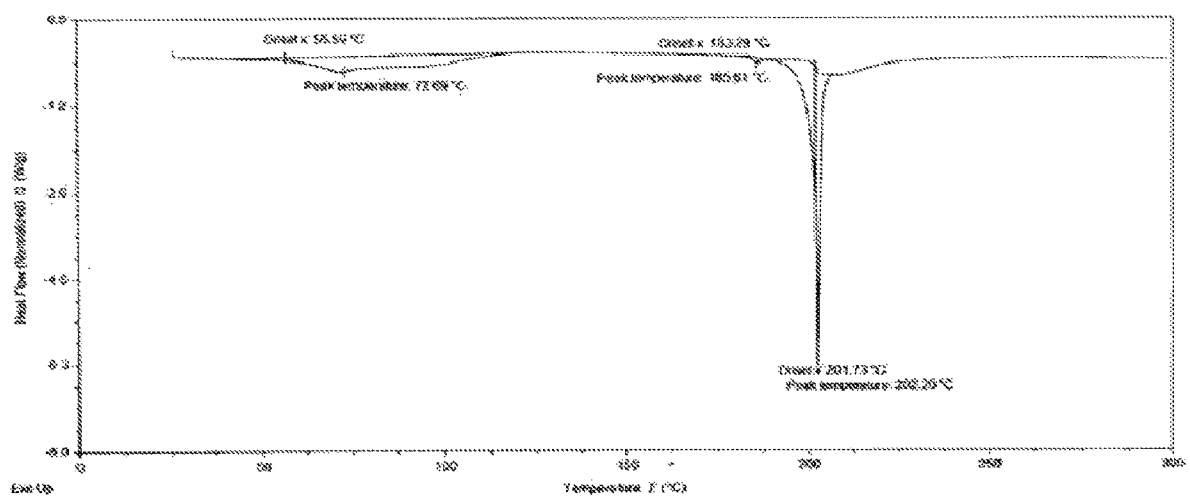

In step-b), the suitable temperature used is ranging from 30° C. to the reflux temperature of the solvent used;

The seventh aspect of the present invention is to provide crystalline Form-N of Ribociclib succinate compound of formula-1a, which is characterized by:
i) Its powder X-ray diffractogram having peaks at about 6.86, 10.05, 10.63, 12.95, 15.56, 16.44, 17.86, 18.26, 20.04, 20.39, 20.76, 21.32, 21.55, 22.07 and 25.12±0.2 degrees 2-theta;
ii) powdered X-ray diffraction pattern as shown in FIG. 6;
iii) its DSC thermogram of crystalline Form-N of Ribociclib succinate as shown in FIG. 7.

Further, the present invention also provides a process for the preparation of crystalline Form-N of Ribociclib succinate compound of formula-1a, comprising of:
a) Suspending Ribociclib compound of formula-1 in a suitable solvent,
b) heating the reaction mixture to a suitable temperature,
c) adding a solution of succinic acid in a solvent to the reaction mixture,
d) cooling the reaction mixture to a suitable temperature,
e) filtering the obtained solid to get the crystalline form-N of Ribociclib succinate compound of formula-1a.

Wherein in step-a) & c), the suitable solvent is selected from ether solvents, chloro solvents, ester solvents, alcohol solvents, ketone solvents, polar aprotic solvents, hydrocarbon solvents, nitrile solvents and polar solvents such as water or mixtures thereof.

In step-b), the suitable temperature used is ranging from 30° C. to the reflux temperature of the solvent used;

In a preferred embodiment of the present invention provides a process for the preparation of crystalline Form-N of Ribociclib succinate compound of formula-1a, comprising of:
a) Suspending Ribociclib compound of formula-1 in tetrahydrofuran,
b) heating the reaction mixture to 60-65° C.,
c) adding an aqueous tetrahydrofuran solution of succinic acid to the solution obtained in step-(b),
d) cooling the reaction mixture to 25-35° C.,
e) filtering the obtained solid to get the crystalline form-N of Ribociclib succinate compound of formula-1a.

The crystalline forms A, B, C, D, E & N of Ribociclib succinate of the present invention are useful for the preparation of pharmaceutical compositions.

The process for the preparation of Ribociclib succinate compound of formula-1a is schematically represented in Scheme-I as below: Scheme-I:

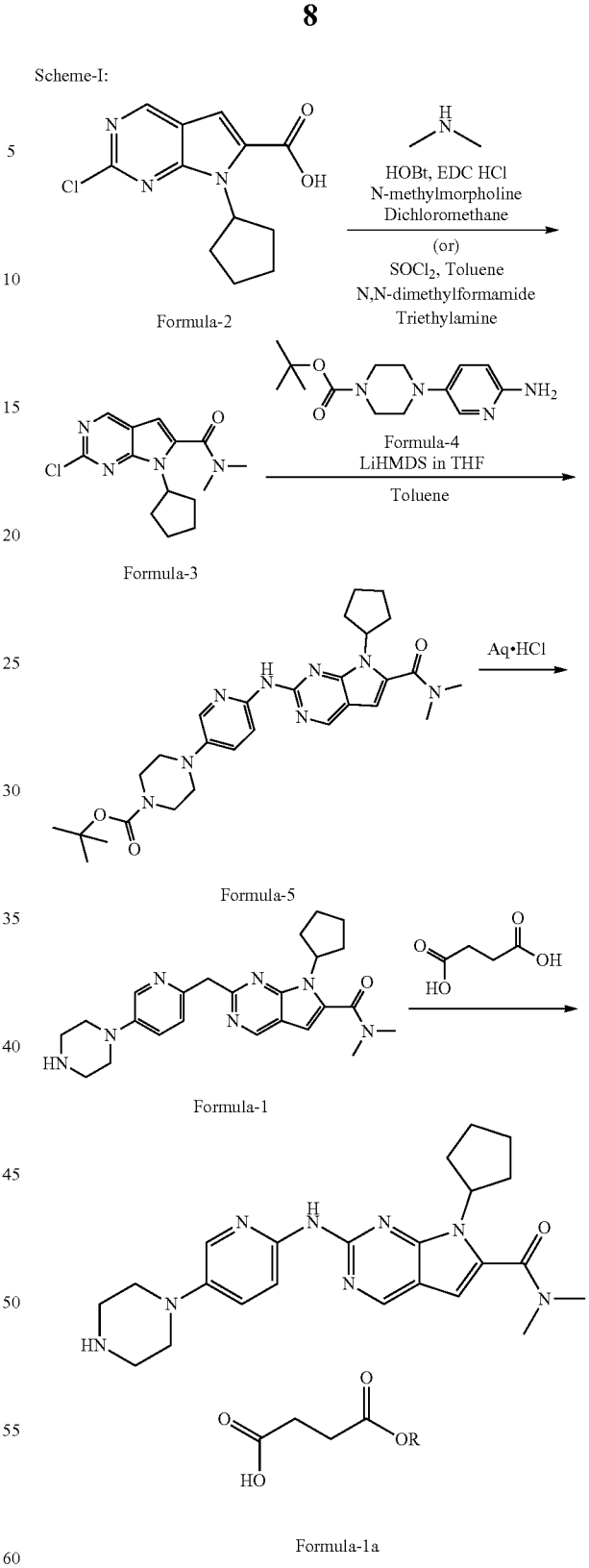

PXRD Method of Analysis:

PXRD analysis of the crystalline forms of Ribociclib succinate compound of formula-1a were carried out using Panlytical Expert Pro DY3248 X-ray powder diffractometer using Cu-Ka radiation of 10 wavelength 1.5406 A° and at continuous scan speed of 0.03°/min.

DSC Method of Analysis:

Differential scanning calorimetric (DSC) analysis was performed with TA/2500 Discovery. Samples of about 2 to 3 milligrams held in a Tzero Aluminum Hermetic closed pan were analyzed at a heating rate of 10° C. per minute.

The best mode of carrying out the present invention was illustrated by the below mentioned examples. These examples are provides as illustration only and hence should not be construed as limitation of the scope of the invention.

Examples

Example-1: Preparation of 2-chloro-7-cyclopentyl-N,N-dimethyl-pyrrolo[2,3-d]pyrimidine-6-carboxamide (Formula-3)

Methylene chloride (1000 mL) and 2-Chloro-7-cyclopentyl-7H-pyrrolo[2,3-d]pyrimidine-6-carboxylic acid (50.0 g, 0.188 moles) were charged into 2 L 4N RB flask under nitrogen atmosphere, and stir of 5-10 min to get brown colored suspension. Reaction mass was cooled to 0±2° C. HOBt (28.0 g, 0.207 moles), EDC.HCl (39.7 g, 0.207 moles) were charged into the reaction mass and stir for 5-10 min at 0±2° C. Dimethylamine 2M solution in ethanol (139.0 mL, 0.282 moles) added dropwise to the reaction mass through addition funnel by maintaining mass temperature at 0±2° C. Then reaction mass was stirred for 5-10 min at 0±2° C. Reaction mass temperature was raised to 30±5° C. and stirred for 7-8 h.

After completion of reaction (by TLC) solvent was distilled off under vacuum on rotavapor at 40° C. to yield brown colored oily crude. The resulting crude was dissolved in ethyl acetate (1500.0 mL) and stirred for 5-10 min at 25-35° C. to get brown colored clear solution. DM water (500.0 mL) was charged to the reaction mass and stirred for 5-10 min. Layers were separated, organic layer was washed with aq. potassium carbonate solution (10 g of potassium carbonate was dissolved in 500.0 mL of DM water). Followed by DM water (500.0 mL) and layers were separated. Organic layer was dried over sodium sulphate and filtered. Solvent from the filtrate was distilled off completely under vacuum at 50° C. on rotavapor to obtain brown colored oily crude. n-Heptane (100 mL) was charged to the oily crude and again solvent was distilled off. The resulting oily crude was leached with n-heptane (250.0 mL) at 30±5° C. for 1 h. Product was filtered under suction with the help of n-heptane (50 mL). The wet product was dried in hot air oven at 45-50° C. for 6 h to afford title compound. Wt. of the product 43.0 g (78% by theory). Purity by HPLC>98.0%.

$H^1$ NMR (DMSO): δ 8.967 (S, 1H), 6.801 (S, 1H), 4.803 (m, 1H), 3.007-3.051-(S, 6H), 2.182-2.251 (m, 2H), 1.964-2.063 (m, 4H), 1.891-1.945 (m, 2H), 1.607-1.670 (m, 2H); Mass m/z (M+1): 293.1

Example-2: Preparation of tert-butyl 4-[6-[[7-cyclopentyl-6-(dimethylcarbamoyl) pyrrolo[2,3-d]pyrimidin-2-yl]amino]-3-pyridyl]piperazine-1-carboxylate (Formula-5)

Toluene (432.0 mL) and 4-(6-amino-pyridine-3-yl)-piperazine-1-carboxylic acid tert-butyl ester (34.3 g, 0.123 moles) were charged into 2 L 4N RB flask under nitrogen atmosphere at 30±5° C. and stirred for 5-10 min to get brown colored suspension. Reaction mass was cooled to 0±5° C. Lithium hexamethyldisilazane 1M solution in THF (259.0 mL, 0.258 moles) was added dropwise to the reaction mass through addition funnel by maintaining the reaction mass temperature at 0±5° C. And stirred the reaction mass for 10-15 min at 0±5° C. to get clear brown colored solution. Add the solution of 2-chloro-7-cyclopentyl-N,N-dimethyl-pyrrolo[2,3-d]pyrimidine-6-carboxamide (36.0 g, 0.123 moles) in 324.0 mL of toluene dropwise to the reaction mass through addition funnel at 0±5° C. Reaction mass temperature was raised to 25-35° C. and stirred for 1 h for reaction completion.

After completion of reaction (by TLC), solvent was distilled off on rotavapor under vacuum at 55-60° C. to get the brown colored solid. DM water (360.0 mL) and aq. sodium bicarbonate solution (36.0 g of sodium bicarbonate was dissolved in 720.0 mL of DM water) were added to the above solid and stirred for 10-15 min. Then methylene chloride (720 mL) was charged to the above solution and stirred for 5-10 min. Layers were separated. Organic layer washed with DM water (720 mL) and layers Separated. Solvent was distilled off from organic layer completely under vacuum at 45-50° C. on rotavapor to obtain brown colored solid. The solid was leached with methanol (180 mL) at 30±5° C. to afford title compound as pale brown colour solid. Weight of the product: 57.0 g (86.6% by theory). Purity by HPLC>98.0%.

$H^1$ NMR (DMSO-d6): δ 9.412 (S, 1H), 8.167-8.190 (d, 2H), 8.02-8.03 (d, 1H), 7.449-7.479 (dd, 1H), 6.603 (S, 1H), 4.690-4.778 (m, 1H), 3.472-3.484 (d, 4H), 3.062-3.073 (d, 10H), 2.413-2.465 (m, 12H), 1.92-1.991 (m, 4H), 1.427-1.65 (m, 10H); Mass m/z (M+1): 535.25

Example-3: Preparation of Ribociclib (Formula-1)

1,4-Dioxane (300.0 mL) and tert-butyl 4-[6-[[7-cyclopentyl-6-(dimethylcarbamoyl) pyrrolo[2,3-d]pyrimidin-2-yl]amino]-3-pyridyl]piperazine-1-carboxylate (30.0 g, 0.056 moles) were charged into 1 L 4N RB flask under nitrogen atmosphere at 30±5° C. and stirred for 5-10 min. Dilute aq. hydrochloric acid (96.8 mL, 0.56 moles, prepared by diluting 48.4 ml of Conc.HCl with 48.4 ml of DM water) was added as dropwise to the reaction mass through addition funnel at 30±5° C. Reaction mass was stirred for 6-7 h for reaction completion.

After reaction completion (by TLC), reaction mass was diluted with DM water (1200 mL) and stirred for 5-10 min. Reaction mass was washed three times with ethyl acetate (300 mL×3) and layers were separated. Aqueous layer pH was adjusted to 10-11 using aq. NaOH (40.0 g of NaOH was dissolved in 800.0 mL of DM water) and stirred the reaction mass for 1 h at 30±5° C. Product was filtered under suction with the help of DM water (60 mL) and wet product was slurry washed with IPA (30 mL). Product was recrystallized from isopropyl alcohol and dried in hot air oven for 6 h at 70-75° C. Weight of the product: 19.2 g (78.8% by theory). Purity by HPLC>99.0%.

$H^1$ NMR (DMSO-d6): δ 9.310 (S, 1H), 8.757 (S, 1H), 8.127-8.150 (d, 1H), 7.974-7.981 (d, 1H), 6.596 (S, 1H), 4.685-4.773 (m, 1H), 3.008-3.050 (m, 10H), 2.835-2.859 (m, 4H), 2.330-2.461 (m, 4H), 1.977-1.990 (m, 4H), 1.631-1.644 (m, 2H); Mass m/z (M+1): 435.24

Example-4: Preparation of Polymorphic Form-A of Ribociclib Succinate (Formula-1a)

Tetrahydrofuran (120 mL) and Ribociclib (3.0 g, 0.0069 moles) were charged into 250 mL 4 neck round bottomed flask at 30±5° C. and stirred for 5-10 min. to get cream colored suspension. Reaction mass was heated to 65-70° C. and stirred for 15 min. to get clear solution. The solution of succinic acid (0.85 g, 0.0072 moles) in tetrahydrofuran (60 mL) was added to the above reaction mass dropwise through addition funnel at 65-70° C. After addition of succinic acid solution, pale yellow coloured suspension was formed in the reaction mass and was stirred for 1 h. Then the reaction mass was cooled to 25-35° C. and stirred for 1 h. Product was filtered off under suction. Product was dried in vacuum oven at 65-70° C. to afford title compound as cream coloured solid. Weight of the product: 3.7 g (97.1% by theory) as cream coloured solid. Purity by HPLC>99.0%.

The obtained crystalline compound is characterized by PXRD as illustrated in FIG. 1.

Example-5: Preparation of Polymorphic Form-B of Ribociclib Succinate (Formula-1a)

Methanol (90 mL) and Ribociclib (3.0 g, 0.0069 moles) were charged into 250 mL 4 necked round bottomed flask and stirred at 30±5° C. for 5-10 min. Reaction mass was heated to 65-70° C. and stirred to get clear solution. Then the solution of succinic acid (0.85 g, 0.0072 moles) in methanol (30 mL) was added to the reaction mass dropwise through addition funnel at 65-70° C. and stirred for 1 h. Reaction mass was cream coloured hazy solution. Then reaction mass was cooled to 25-35° C. and stirred for 1 h. Product was filtered under suction and dried in vacuum oven at 65-70° C. to afford title compound as cream coloured solid. Weight of the product: 3.2 g (84.0% by theory). Purity by HPLC>99.0%.

The obtained crystalline compound is characterized by PXRD as illustrated in FIG. 2.

Example-6: Preparation of Polymorphic Form-C of Ribociclib Succinate (Formula-1a)

Ethanol (135 mL) and Ribociclib (3.0 g, 0.0069 moles) were charged into 250 ml 4 necked round bottomed flask and stirred at 30±5° C. for 5-10 min. Reaction mass was heated to 70-75° C. to get clear solution. Then the solution of Succinic acid (0.85 g, 0.0072 moles) in ethanol (15 mL) dissolved at 70-75° C. was added dropwise through addition funnel to the above solution at 70-75° C. and then stirred for 1 h. Reaction mass was pale cream coloured hazy solution. Reaction mass was cooled to 25-35° C. and stirred for 1 h 30 min. Product was filtered from the resulting suspension under suction and dried in vacuum oven at 65-70° C. to afford title compound as cream coloured solid. Weight of the product: 3.0 g (78.7% by theory). Purity by HPLC>99.0%.

The obtained crystalline compound is characterized by PXRD as illustrated in FIG. 3.

Example-7: Preparation of Polymorphic Form-D of Ribociclib Succinate (Formula-1a)

n-Butanol (75 mL) and Ribociclib (3.0 g, 0.0069 moles) were charged in to 250 mL 4 neck round bottomed flask and stirred at 30±5° C. for 5-10 min. Reaction mass was heated to 70-75° C. and stirred for 20 min and filtered to get clear solution. The filtrate was transferred into 250 mL 4 neck round bottomed flask and heated to 70-75° C. Then the solution of succinic acid (0.85 g, 0.0072 moles) in n-Butanol (15 mL) dissolved at 70-75° C. was added dropwise to the reaction mass at 70-75° C. and stirred for 1 h. Reaction mass was cooled to 25-35° C. and stirred for 1 h. Product was filtered off under suction and dried in vacuum oven at 65-70° C. to get the title compound as cream coloured solid. Weight of the product: 3.0 g (78.7% by theory). Purity by HPLC>99.0%.

The obtained crystalline compound is characterized by PXRD as illustrated in FIG. 4.

Example-8: Preparation of Polymorphic Form-E of Ribociclib Succinate (Formula-1a)

Methylene chloride (40 mL) and Ribociclib (2.0 g, 0.0046 moles) were charged in to 250 mL 4 neck round bottomed flask at 30±5° C. and stirred for 5-10 min. Reaction mass was heated to 35-40° C. and stirred for 30 min. to get clear solution. The succinic acid (0.57 g, 0.0048 moles) solution in tetrahydrofuran (10 mL) was added dropwise to the reaction mass at 35-40° C. Reaction mass was turned to cream coloured suspension and was stirred for 1 h. Reaction mass was cooled to 25-35° C. and stirred for 1 h. Product was filtered off under suction and dried in vacuum oven at 65-70° C. to yield the title compound as cream coloured solid. Weight of the product: 2.2 g (86.6% by theory). Purity by HPLC>99.0%.

The obtained crystalline compound is characterized by PXRD as illustrated in FIG. 5.

Example-9: Preparation of 2-chloro-7-cyclopentyl-N,N-dimethyl-pyrrolo[2,3-d]pyrimidine-6-carboxamide ((Formula-3)

N,N-Dimethylformamide (150 mL) and 2-Chloro-7-cyclopentyl-7H-pyrrolo[2,3-d]pyrimidine-6-carboxylic acid (50.0 g, 0.188 moles) were charged into 2 L 4N RB flask under $CaCl_2$ guard tube condition, and stirred of 5-10 min to get cream colored suspension. Reaction mass was cooled to 0-5° C. HOBt (28.0 g, 0.207 moles), EDC.HCl (57.7 g, 0.301 moles) were charged into the reaction mass and stirred for 5-10 min at 0-5° C. Dimethylamine 2M solution in THF (141.0 mL, 0.282 moles) was added dropwise to the above reaction mass by maintaining the mass temperature at 0-5° C. Then reaction mass was stirred for 5-10 min at 0-5° C. N-Methylmorpholine (57.1 g, 0.564 moles) was added dropwise to the reaction mass by maintaining mass temperature at 0-5° C. and stirred for 5-10 min at 0-5° C. Reaction mass temperature was raised to 25-35° C. and stirred for 12-15 h.

After completion of reaction (by HPLC), added 1000.0 mL chilled water (5-10° C.) and stirred for 10-15 min. Aq. sodium bicarbonate solution (50 g of sodium bicarbonate was dissolved in 1000.0 mL DM water) was added to the reaction mass and stirred for 1 h to get cream colored suspension. Product was filtered under suction with the help of DM water (500 mL). The wet product leached from DM water (500.0 mL). The wet product was dried in hot air oven at 60-65° C. for 6 h to afford title compound. Wt. of the product 43.0 g (78.2% by theory). Purity by HPLC>99.0%.

Example-10: Preparation of 2-chloro-7-cyclopentyl-N,N-dimethyl-pyrrolo[2,3-d]pyrimidine-6-carboxamide (Formula-3)

Toluene (500 mL) and 2-Chloro-7-cyclopentyl-7H-pyrrolo[2,3-d]pyrimidine-6-carboxylic acid (100.0 g, 0.377 moles) were charged into 2 L 4N RB flask under $CaCl_2$ guard tube condition, and stirred of 5-10 min to get cream colored suspension. Added N,N-dimethylformamide (10.0 mL) and stirred for 5-10 min. Charged thionyl chloride (67.2 g, 0.566 moles) to the reaction mass and stir for 5-10 min. at 25-35° C. to get pale brown colored suspension. Reaction mass was heated to 75-80° C. and stirred for 3-4 h. After completion of reaction (by HPLC), cooled to 0-5° C. to become brown colored suspension. Mixture of 2M solution of dimethylamine in THF (470.0 mL, 0.942 moles) and triethylamine (122.0 g, 1.20 moles) added dropwise to the reaction mass through addition funnel by maintaining the mass temperature at 0-10° C. and then stirred for 5-10 min. Reaction mass temperature was raised to 25-35° C. and stirred for 1-2 h. After completion of reaction (by HPLC) solvent was distilled off under vacuum on rotavapor at 60-65° C. to yield brown colored crude. The resulting crude was dispersed in DM water (1000.0 mL) and stirred for 1 h at 25-35° C. to get cream colored suspension. Product was filtered under suction with the help of DM water (500 mL). The wet product was dried in hot air oven at 60-65° C. for 6 h to afford the title compound. Wt. of the product 106.0 g (96.4% by theory). Purity by HPLC>99.0%.

Example-11: Preparation of tert-butyl 4-[6-[[7-cyclopentyl-6-(dimethyl carbamoyl)pyrrolo[2,3-d] pyrimidin-2-yl]amino]-3-pyridyl]piperazine-1-carboxylate (Formula-5)

Toluene (300.0 mL) and 4-(6-amino-pyridine-3-yl)-piperazine-1-carboxylic acid tert-butyl ester (95.3 g, 0.342 moles) were charged into 2 L 4N RB flask under nitrogen atmosphere at 25-35° C. and stirred for 5-10 min to get brown colored suspension. Reaction mass was cooled to 0-5° C. Lithium hexamethyldisilazane 1M solution in THF (710.0 mL, 0.718 moles) was added dropwise to the reaction mass through addition funnel by maintaining the reaction mass temperature at 0-10° C. then the reaction mass was stirred for 10-15 min at 0-5° C. to get clear brown colored solution. The solution of 2-chloro-7-cyclopentyl-N,N-dimethyl-pyrrolo[2,3-d]pyrimidine-6-carboxamide (100.0 g, 0.342 moles) in 300.0 mL of toluene was added dropwise to the reaction mass through addition funnel at 0-5° C. After completion of addition reaction mass temperature was raised to 25-35° C. and stirred for 1 h.

After completion of reaction (by HPLC), reaction mass quenched with DM water (100 mL) by maintaining the reaction mass temperature at 25-35° C. and stirred for 5-10 min. to get brown colored suspension. Solvent was distilled off on rotavapor under vacuum at 60-65° C. to get the brown colored solid. The resulting solid was leached with methanol (800 mL) at 25-35° C. followed by DM water (1000 mL). Solid was filtered and dried in hot air oven at 60-65° C. for 6 h to afford title compound as pale brown color solid. Weight of the product: 142.0 g (77.6% by theory). Purity by HPLC>99.0%.

Example-12: Preparation of Ribociclib (Formula-1)

DM water (200.0 mL) and tert-butyl 4-[6-[[7-cyclopentyl-6-(dimethyl carbamoyl)pyrrolo[2,3-d]pyrimidin-2-yl] amino]-3-pyridyl]piperazine-1-carboxylate (40.0 g, 0.075 moles) were charged into 1 L 4N RB flask at 30±5° C. and stirred for 5-10 min. to get cream colored suspension. Reaction mass was heated to 40-45° C. and diluted aq. hydrochloric acid (199.0 mL, 0.561 moles, prepared by diluting 49.0 mL of Conc. hydrochloric acid with 150 mL of DM water) was added dropwise to the above reaction mass and stirred for about 1 h to get pale brown colored clear solution. Resulting clear solution was further stirred for 1-2 h for reaction completion.

After reaction completion (by HPLC), reaction mass was diluted with DM water (80 mL) and stirred for 5-10 min. Reaction mass was washed with ethyl acetate (200 mL×2) and layers were separated. Aqueous layer was basified using aq. sodium hydroxide solution (45.0 g of sodium hydroxide was dissolved in 900.0 mL of DM water) and stirred the resulting cream colored suspension for 1 h at 25-35° C. Product was filtered under suction with the help of DM water (200 mL). Wet product was leached from DM water (400 mL) followed by methanol (200 mL) and product was filtered and dried in hot air oven for 6 h at 70-75° C. Weight of the product: 29.6 g (91.0% by theory). Purity by HPLC>99.0%.

Example-13: Preparation of Polymorphic Form-N of Ribociclib Succinate (Formula-1a)

Tetrahydrofuran (280 mL) and Ribociclib (7.0 g, 0.0161 moles) were charged into 500 ml 4N round bottomed flask at 30±5° C. and stirred for 5-10 min. to get cream colored suspension. Reaction mass was heated to 60-65° C. and stirred for 15 min. to get clear solution. After clear solution, activated carbon (0.7 g) was charged and stirred for 30 min. Reaction mass was filtered under suction. Filtrate was transferred into fresh 500 ml 4N round bottomed flask and heated to 60-65° C. The aq. tetrahydrofuran solution of succinic acid (prepared by dissolving succinic acid 1.9 g, 0.0161 moles in the solvent mixture of tetrahydrofuran (19.6 ml) and water (3.9 ml)) was added drop wise to the above solution of Ribociclib at 60-65° C. Reaction mass was cooled to 30±5° C. and stirred for 1 h to get off-white to cream colored suspension. Reaction mass was filtered under suction under nitrogen atmosphere and suck dried for 30-45 min. Product was further dried in vacuum oven for 24 h at 50-55° C. to afford title compound. Weight of the product: 7.9 g (88.4% by theory). Purity by HPLC: 99.86%. Mass m/z (M+1): 435.14

$H^1$ NMR (DMSO-d6): δ 9.344 (S, 1H), 8.763 (S, 1H), 8.146-8.169 (d, 1H), S 8.001-8.008 (d, 1H), 7.420-7.450 (dd, 1H), 6.600 (S, 1H), 4.689-4.777 (m, 1H), 3.103-3.128 (m, 4H), 3.056 (m, 5H), 2.963-2.988 (m, 4H), 2.410-2.463 (m, 2H), 2.307 (s, 2H), 1.974-1.980 (m, 4H) 1.634-1.663 (m, 2H).

The obtained crystalline compound is characterized by PXRD as illustrated in FIG. 6 and its DSC thermogram as illustrated in FIG. 7.

The invention claimed is:
1. A process for the preparation of Ribociclib succinate of Formula-1a:

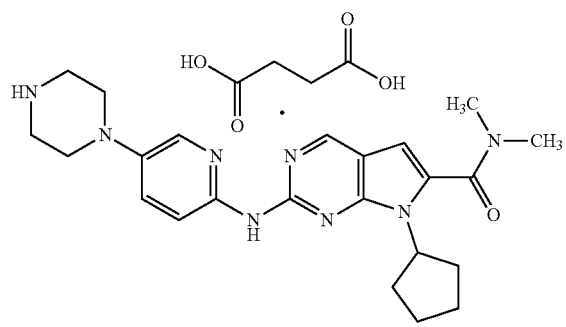

Formula-1a wherein the process comprises the following steps:

a) treating a compound of Formula-2:

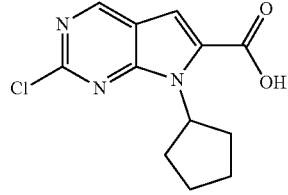

Formula-2 with thionyl chloride, followed by dimethylamine, in the presence of a base in a solvent, to provide a compound of Formula-3:

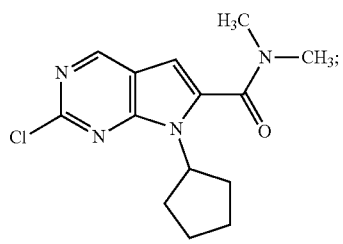

Formula-3 b) reacting the compound of Formula-3 above with a compound of Formula-4:

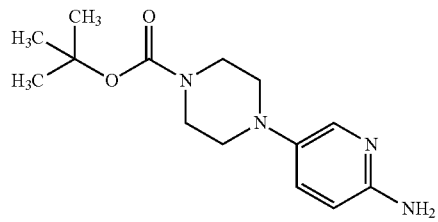

Formula-4 in the presence of an organosilicon base in a solvent, to provide a compound of Formula-5:

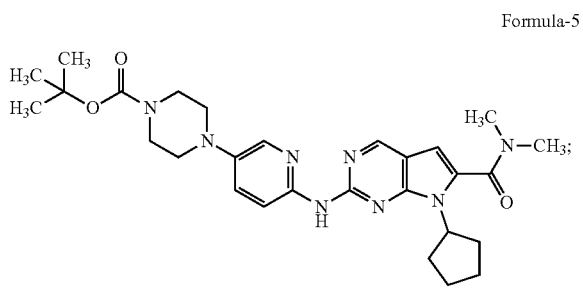 [SMILES: CN(C)C(=O)c1cc2cnc(Nc3ccc(N4CCN(C(=O)OC(C)(C)C)CC4)cn3)nc2n1C1CCCC1]

Formula-5 c) treating the compound of Formula-5 above with aqueous hydrochloric acid, optionally in the presence of a solvent, to provide Ribociclib of Formula-1:

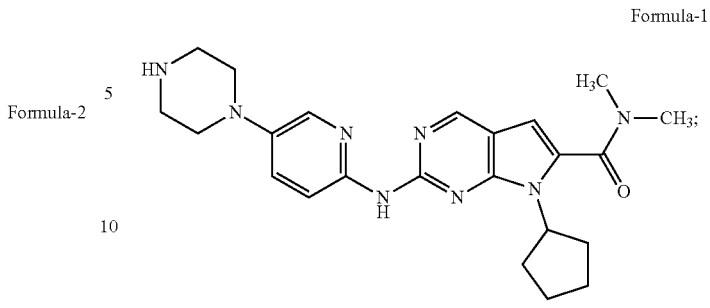

Formula-1 d) optionally purifying the Ribociclib of Formula-1 provided above with a solvent; and e) treating the Ribociclib of Formula-1 provided in step c) or step d) above, with succinic acid in a solvent, or a mixture of solvents, to provide Ribociclib succinate of Formula-1a:

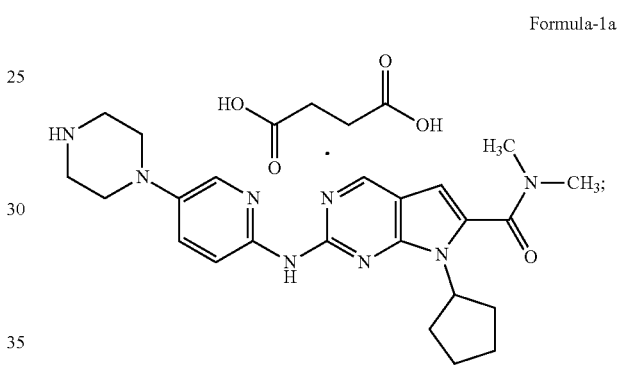

Formula-1a wherein:
in step a), the base is selected from the group consisting of diethylamine, diisobutylamine, diisopropylamine, diisopropylethylamine, dimethylamine, 4-(dimethylamino)pyridine, lithium amide, lithium tert-butoxide, lithium carbonate, lithium diisopropylamide, lithium hexamethyldisilazide, lithium hydride, lithium hydroxide, 2,6-lutidine, N-methylmorpholine, potassium amide, potassium bicarbonate, potassium tert-butoxide, potassium carbonate, potassium ethoxide, potassium hexamethyldisilazide, potassium hydride, potassium hydroxide, potassium methoxide, pyridine, sodium amide, sodium bicarbonate, sodium tert-butoxide, sodium carbonate, sodium ethoxide, sodium hexamethyldisilazide, sodium hydride, sodium hydroxide, sodium methoxide, and triethylamine, or a mixture thereof;

in step b), the organosilicon base is selected from the group consisting of lithium hexamethyldisilazide, sodium hexamethyldisilazide, and potassium hexamethyldisilazide, or a mixture thereof; and in step a), step b), step c), step d), and step e), the solvent is independently selected from the group consisting of acetone, acetonitrile, benzene, n-butanol, tert-butanol carbon tetrachloride, chloroform, cyclohexane, dichloroethane, dichloromethane, diethyl ether, diglyme, diisopropyl ether, 1,2-dimethoxyethane, dimethyl ether, N,N-dimethylacetamide, N,N-dimethylformamide, dimethylsulfoxide, 1,4-dioxane, ethanol, ethyl acetate, n-butyl acetate, n-heptane, n-hexane, isobutanol, isobutyronitrile, isopropanol, isopropyl acetate, methanol, methyl acetate, methyl ethyl ketone, methyl isobutyl ketone, N-methylpyrrolidone, methyl tert-butyl ether, monoglyme, petroleum ether, n-propanol, propionitrile, tetrahydrofuran, toluene, water, and xylene, or a mixture thereof.

2. The process as claimed in claim 1, wherein the process comprises the following step:
a) treating a compound of Formula-2:

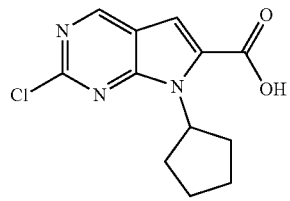

Formula-2 with thionyl chloride, followed by dimethylamine, in the presence of triethylamine in a mixture of tetrahydrofuran and toluene, to provide a compound of Formula-3:

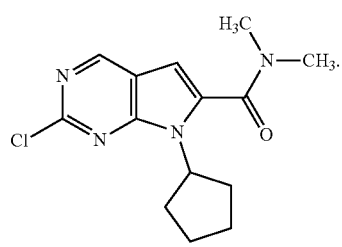

Formula-3

3. The process as claimed in claim 1, wherein the process comprises the following step:
b) reacting a compound of Formula-3:

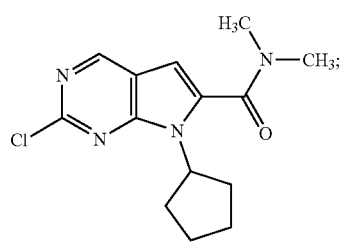

Formula-3 with a compound of Formula-4:

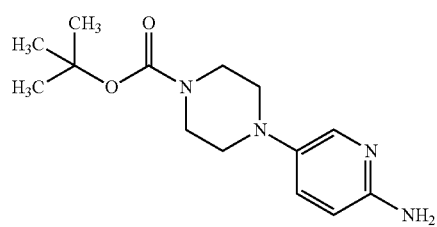

Formula-4 in the presence of lithium hexamethyldisilazide in toluene, to provide a compound of Formula-5:

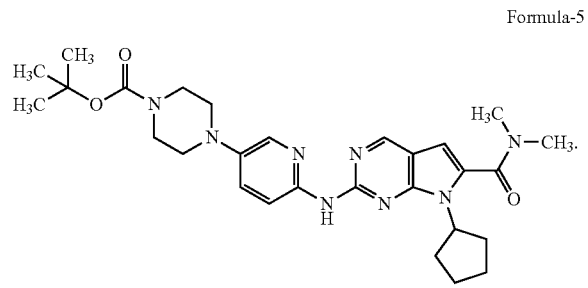 [SMILES: CN(C)C(=O)c1cc2cnc(Nc3ccc(N4CCN(C(=O)OC(C)(C)C)CC4)cn3)nc2n1C1CCCC1]

Formula-5

4. The process as claimed in claim 1, wherein the process comprises the following step:
c) treating a compound of Formula-5:

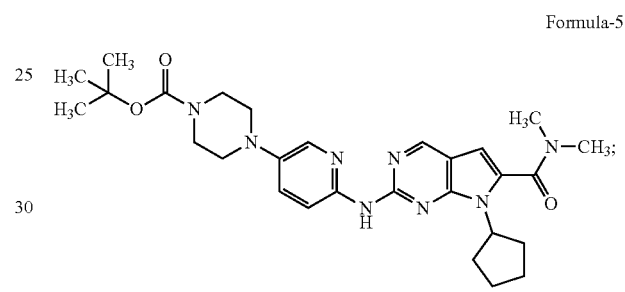

Formula-5 with aqueous hydrochloric acid, to provide Ribociclib of Formula-1:

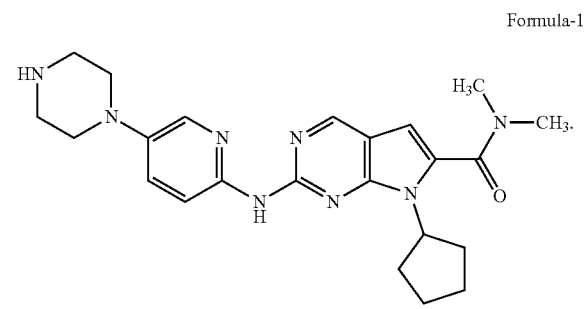 [SMILES: CN(C)C(=O)c1cc2cnc(Nc3ccc(N4CCNCC4)cn3)nc2n1C1CCCC1]

Formula-1

5. The process as claimed in claim 1, wherein the process comprises the following steps:
a) treating a compound of Formula-2:

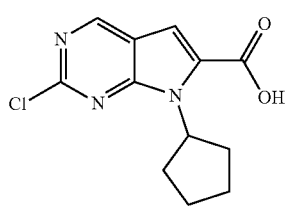

Formula-2 with thionyl chloride, followed by dimethylamine, in the presence of triethylamine in a mixture of tetrahydrofuran and toluene, to provide a compound of Formula-3:

Formula-3

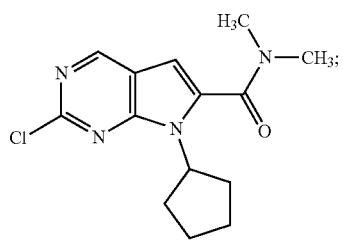

b) reacting the compound of Formula-3 above with a compound of Formula-4:

Formula-4

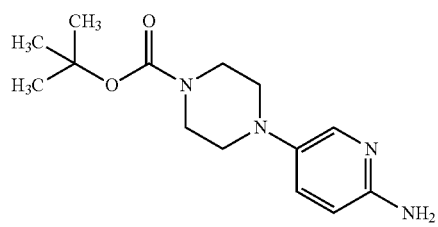

in the presence of lithium hexamethyldisilazide in toluene, to provide a compound of Formula-5:

Formula-5

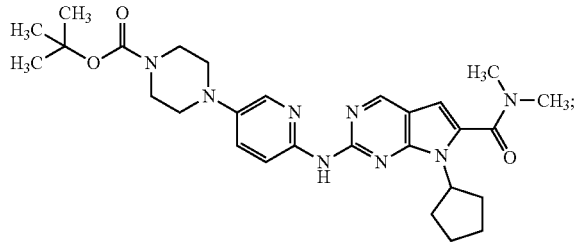

c) treating the compound of Formula-5 above with aqueous hydrochloric acid, to provide Ribociclib of Formula-1:

Formula-1

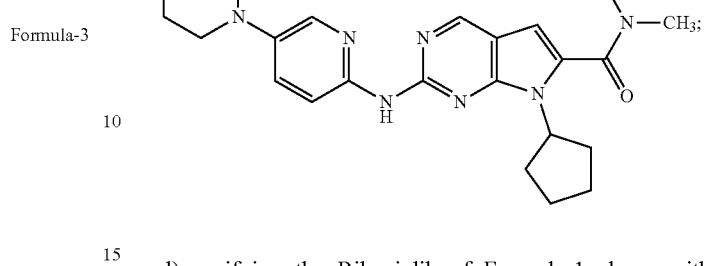

d) purifying the Ribociclib of Formula-1 above with methanol; and e) treating the Ribociclib of Formula-1 provided in step d) above, with succinic acid in aqueous tetrahydrofuran, to provide Ribociclib succinate of Formula-1a:

Formula-1a

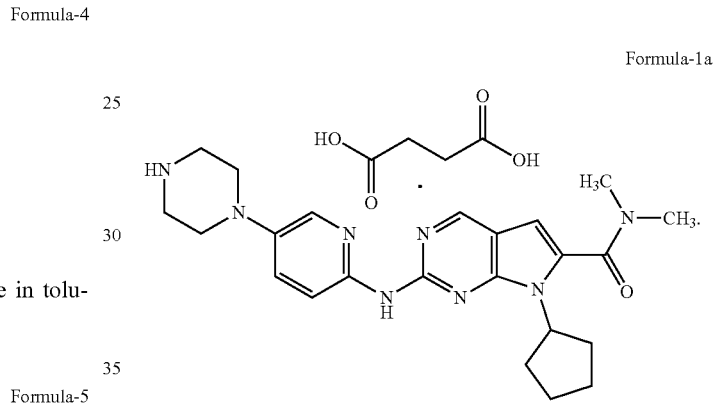

6. The process as claimed in claim 1, wherein in step a), the base is selected from the group consisting of diethylamine, diisobutylamine, diisopropylamine, diisopropylethylamine, dimethylamine, and triethylamine.

7. The process as claimed in claim 1, wherein in step b), the organosilicon base is lithium hexamethyldisilazide.

8. The process as claimed in claim 1, wherein in step a), step b), step c), step d), and step e), the solvent is independently selected from the group consisting of methanol, tetrahydrofuran, toluene, and water, or a mixture thereof.

\* \* \* \* \*